(12) United States Patent
Vu (10) Patent No.: US 9,566,133 B2
(45) Date of Patent: Feb. 14, 2017

(54) METHOD FOR SHAPING AN ORTHODONTIC WIRE MADE OF A SHAPE-MEMORY MATERIAL, AND ASSOCIATED WIRE

(75) Inventor: Hoang Viet-Ha Julius Vu, Unna (DE)

(73) Assignee: DW LINGUAL SYSTEMS GMBH, Bad Essen (DE)

( * ) Notice: Subject to any disclaimer, the term of this patent is extended or adjusted under 35 U.S.C. 154(b) by 56 days.

(21) Appl. No.: 14/238,362

(22) PCT Filed: Aug. 2, 2012

(86) PCT No.: PCT/EP2012/065190
§ 371 (c)(1),
(2), (4) Date: Apr. 23, 2014

(87) PCT Pub. No.: WO2013/023935
PCT Pub. Date: Feb. 21, 2013

(65) Prior Publication Data
US 2014/0234794 A1    Aug. 21, 2014

(30) Foreign Application Priority Data
Aug. 17, 2011   (DE) ......................... 10 2011 081 151

(51) Int. Cl.
*A61C 7/20* (2006.01)
*A61C 7/00* (2006.01)
(Continued)

(52) U.S. Cl.
CPC ................. *A61C 7/002* (2013.01); *A61C 7/20* (2013.01); *A61C 7/282* (2013.01); *A61C 9/004* (2013.01);
(Continued)

(58) Field of Classification Search
CPC .................................................... A61C 7/20
(Continued)

(56) References Cited

U.S. PATENT DOCUMENTS 4,037,324 A * 7/1977 Andreasen ............... A61C 7/12
433/24
5,456,600 A   10/1995 Andreiko et al.
(Continued)

FOREIGN PATENT DOCUMENTS

DE            195 40 755      8/1997
DE         10 2006 048063     4/2006
(Continued)

OTHER PUBLICATIONS

Imai, Sadao, "Notification of Reasons for Refusal in Application No. JP 2014-525394", Japanese Patent Office, Apr. 20, 2016, 6 pages.

*Primary Examiner* — Ralph Lewis
(74) *Attorney, Agent, or Firm* — Greer, Burns & Crain, Ltd.; Steven P. Fallon (57) ABSTRACT

Method for shaping an orthodontic wire, made of a shape-memory material, into a target geometry in order to permit precise insertion into a patient-specific orthodontic apparatus, said method having the following steps: a) creating a patient-specific target set-up of the upper jaw or lower jaw of the patient, b) placing brackets on teeth to be treated in the target set-up, c) preparing a two-dimensional image of the target set-up with brackets in a plan view, d) loading the image into a data processor, e) identifying the position of the slots of the brackets in the image, f) exporting data on the position of the slots from the data processor, g) creating a baking mold for the shape-memory wire, wherein the data are used to help generate wire-fixing portions in the baking mold that maintain the wire in areas corresponding to the slots during the baking, h) inserting the wire into the baking mold, and i) baking the wire.

21 Claims, 7 Drawing Sheets

(51) Int. Cl.
*A61C 7/28* (2006.01)
*A61C 9/00* (2006.01)
*A61C 13/00* (2006.01)

(52) U.S. Cl.
CPC ...... *A61C 13/0004* (2013.01); *A61C 2201/007* (2013.01)

(58) Field of Classification Search
USPC .......................................................... 433/20
See application file for complete search history.

(56) References Cited

U.S. PATENT DOCUMENTS

| | | | |
|---|---|---|---|
| 6,928,733 B2 * | 8/2005 | Rubbert | A61C 7/20 29/407.04 |
| 2004/0083611 A1 | 5/2004 | Rubbert | |
| 2008/0254403 A1 | 10/2008 | Hilliard | |

FOREIGN PATENT DOCUMENTS

| | | |
|---|---|---|
| DE | 698 15 155 T2 | 3/2007 |
| JP | H08508174 A | 9/1996 |
| JP | 2004195152 A | 7/2004 |
| JP | 2008110203 A | 5/2008 |
| WO | WO 99/34747 | 7/1999 |

\* cited by examiner

| | 47 | 46 | 45 | 44 | 43 | 42 | 41 | 31 | 32 | 33 | 34 | 35 | 36 | 37 |
|---|---|---|---|---|---|---|---|---|---|---|---|---|---|---|
| mesial(+), distal(−), [mm] | | | | | | | | | | | | | | |
| buccal(+), lingal(−), [mm] | | | | | | | | | | | | | | |
| rotation mesial(+), distal(−), [°] | | | | | | | | | | | | | | |
| sliding pathway mesial [mm] | | | | | | | | | | | | | | |
| sliding pathway distal [mm] | | | | | | | | | | | | | | |
| straight wire sections [mm] | | | | | | | | | | | | | | |

METHOD FOR SHAPING AN ORTHODONTIC WIRE MADE OF A SHAPE-MEMORY MATERIAL, AND ASSOCIATED WIRE

FIELD

The invention relates to a method for shaping an orthodontic wire made of a shape memory material and a corresponding wire. Moreover, the invention relates to a method for producing an orthodontic wire by means of the method.

BACKGROUND

Brackets are glued on the teeth of the patient to be treated and connected to one another via an orthodontic wire, for the orthodontic treatment of patients having fixed braces. The brackets present a pad for connection with the tooth and a bracket body which receives the archwire.

Orthodontic wires made of a shape memory material are often inserted into the brackets, to start an orthodontic treatment to achieve a "rough" orientation of the teeth. It is only towards the end of the orthodontic treatment that for instance steel wires are used to move the teeth as precisely as possible into a defined position.

The orthodontic wires must have a certain geometry (target geometry) to be able to transmit the desirable strength to the brackets and hence to the teeth. It is known to shape orthodontic wires of steel into the desirable target geometry using pliers.

This does not work with orthodontic wires made of a shape memory material since they do not present the conventional elasticity during deformation.

The main shape memory materials include the Cu—Zn—X (X: Si, Sn, Al) alloys and the intermetallic NiTi alloy (nickel content of approx. 55 weight percent) whereas the NiTi alloy could take on a greater technological significance due to its more favourable properties. The shape memory effect rests on a thermoelastic martensite transformation, on a reversible phase transformation conditioned by shearing the grid planes. The cooling down of the high-temperature phase, called austenite, below the alloy-specific martensite start temperature leads to the phase transformation without form-change and without irreversible plastic deformation, as is the case with steels. Shape memory alloys can be easily deformed in martensitic condition; the reversible deformation can amount to 8% with NiTi. This deformation is durable as long as the alloy is in martensitic condition. Warming-up to a temperature above the alloy-specific austenite start temperature leads then to resetting the original shape.

Document DE 195 40 755 C2 describes the generic manufacture of an archwire made of shape memory material by plastering transfer elements which are inserted in slots of brackets on a model of a target configuration, by loosening the transfer elements from the slots, by replacing sections of the transfer elements with wire reception devices and arranging an archwire into said sections followed by warming-up to achieve durable deformation.

To shape an orthodontic wire made of a shape memory material into a target geometry, said wire is given the desirable target geometry in a special baking mould and then heated up to a specific transition temperature for the shape memory material. The orthodontic wire is subsequently cooled down again and inserted into an orthodontic apparatus of a patient, for instance fixed lingual or buccal brackets, under deformation. The orthodontic wire is again warmed up in the patient's mouth and remembers its target geometry into which the wire then strives to re-deform. The orthodontic wire exerts a force on the brackets during said deformation through which the corresponding teeth are moved.

A shortcoming during the deformation of an orthodontic wire made of a shape memory material to achieve a target geometry lies in that the method is quite wasteful and hence quite costly.

Document DE 698 15 155 T2 describes the calculation of forces which should be exerted by an archwire, in a virtual model.

SUMMARY

The object of the present invention is then to provide an alternative method for producing an orthodontic wire made of shape memory material with a target geometry, in particular a simpler and more cost efficient method which leads to an orthodontic wire made of a shape memory material with a target geometry.

The object of the invention is satisfied with a process exhibiting the features of claim 1 which provides a corresponding orthodontic wire according to its independent claim.

In step 1a) a target set-up is advantageously made of plaster or is a virtual target set-up.

In step 1b) preferably lingual brackets are arranged on the teeth of the target set-up to be treated.

In step 1c) a two-dimensional photo is advantageously prepared, in particular by using a camera with optics.

For step 1c) a light band is preferably projected into the target set-up, the band showing the focal plane of the optics for preparing the photo and the light band is again preferably projected into the slot plane which enables to represent the slots clearly in the image.

A digital photo is preferably prepared in step 1c).

In step 1d), a digital photo or a scan of an analogue photo is advantageously loaded into the data processing unit.

A computer, in particular a desktop PC is used preferably as a data processing unit.

The identification in step 1e) advantageously takes place manually or automatically, in particular using morphing algorithms.

After the identification in step 1e) the position of at least one slot is advantageously modified manually in the occlusal plane, in particular towards the mesial, distal, lingual or buccal or combinations thereof, in particular rotations.

After the identification in step 1e) the length of at least one slot is preferably increased or decreased mesially and/or distally.

Exporting in step 1f) advantageously is the writing of the data into a computer file.

In step 1g) a baking mould is advantageously made of a metal plate, in particular of steel or aluminium.

In step 1g), the wire-fixing portions for the wire are advantageously milled into the metal plate or into the metal strip, respectively, and respectively a free space is milled for the wire between neighbouring wire-fixing portions, in which the wire is not held.

The bottoms of the wire-fixing portions and the bottoms of the free spaces are advantageously milled to the same height by which the wire may be inserted flat into the baking mould.

The wire in step 1h) is preferably inserted manually into the baking mould.

BRIEF DESCRIPTION OF THE DRAWINGS

Additional characteristics, details and advantages of the invention can be seen in the claims and the following description of preferred embodiments as well as using the drawings. The figures show schematically:

DETAILED DESCRIPTION OF PREFERRED EMBODIMENTS

Figure 1:
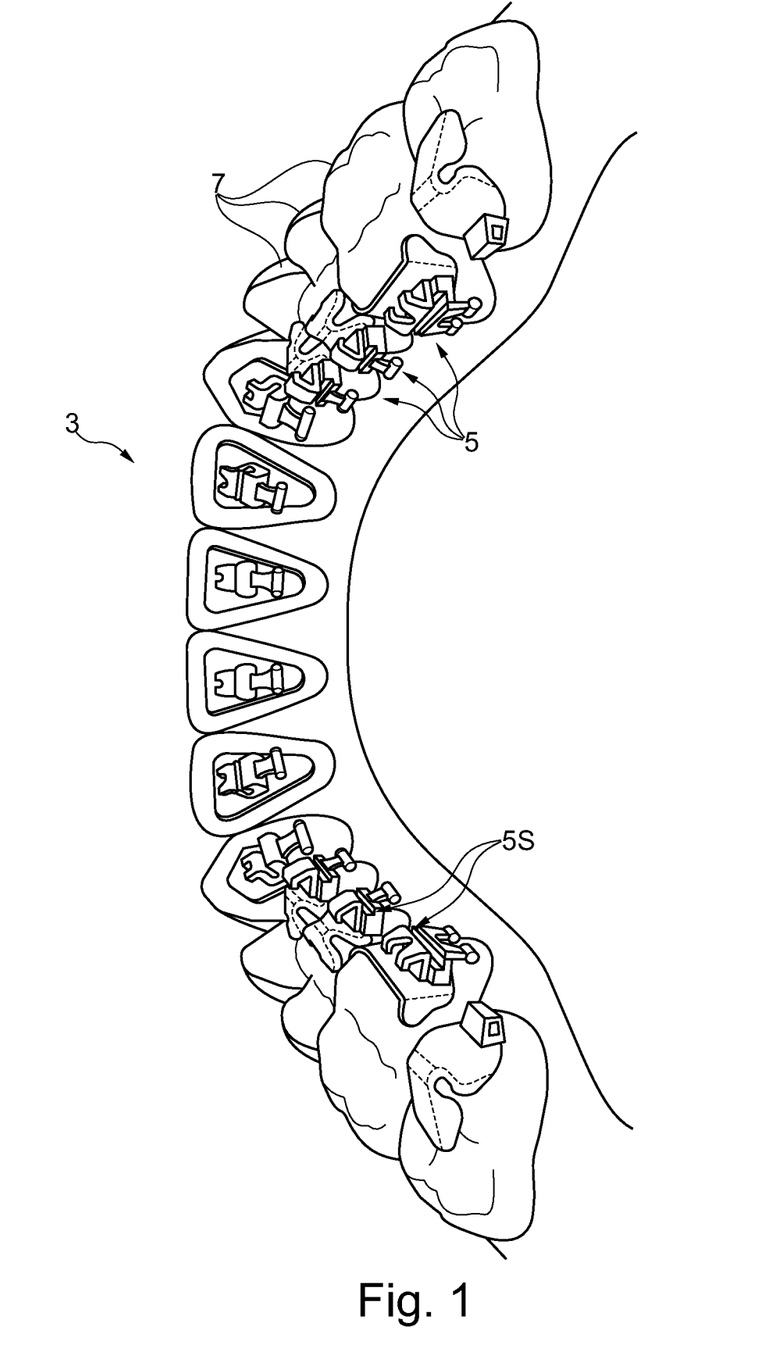
FIG. 1 shows a perspective view of a target set-up with brackets.

A plaster cast of a patient's lower jaw is produced, who shall be treated orthodontically. The plaster cast is sawed up wherein the teeth are separated. Subsequently, the teeth are arranged in a target set-up 3, see FIG. 1, which shall represent the desirable result at the end of the treatment. Lingual brackets 5 are glued on the teeth 7 in the target set-up 3 of FIG. 1. At the end of the orthodontic treatment, all the slots 5S of the lingual brackets 5 shall lie substantially in one plane, the so-called slot plane, as is shown in FIG. 1.

A photo is generated of the top view of the target set-up 3 of FIG. 1 as follows (schematically in FIG. 2): The target set-up 3 is arranged centrally under a dome lighting so as to provide uniform illumination of said set-up. A camera with optics is adjusted on the target set-up 3 in order to take a photo of the top view of the same.

A projector for a laser band 17 is associated with the camera, wherein the laser band 17 shows the focal plane of the optics of the camera. The vertical height of the target set-up 3 is adjusted using the laser band 17 in such a way that the slot plane of the lingual brackets 5 of the target set-up 3 is on a vertical height with the laser band 17.

Figure 2:
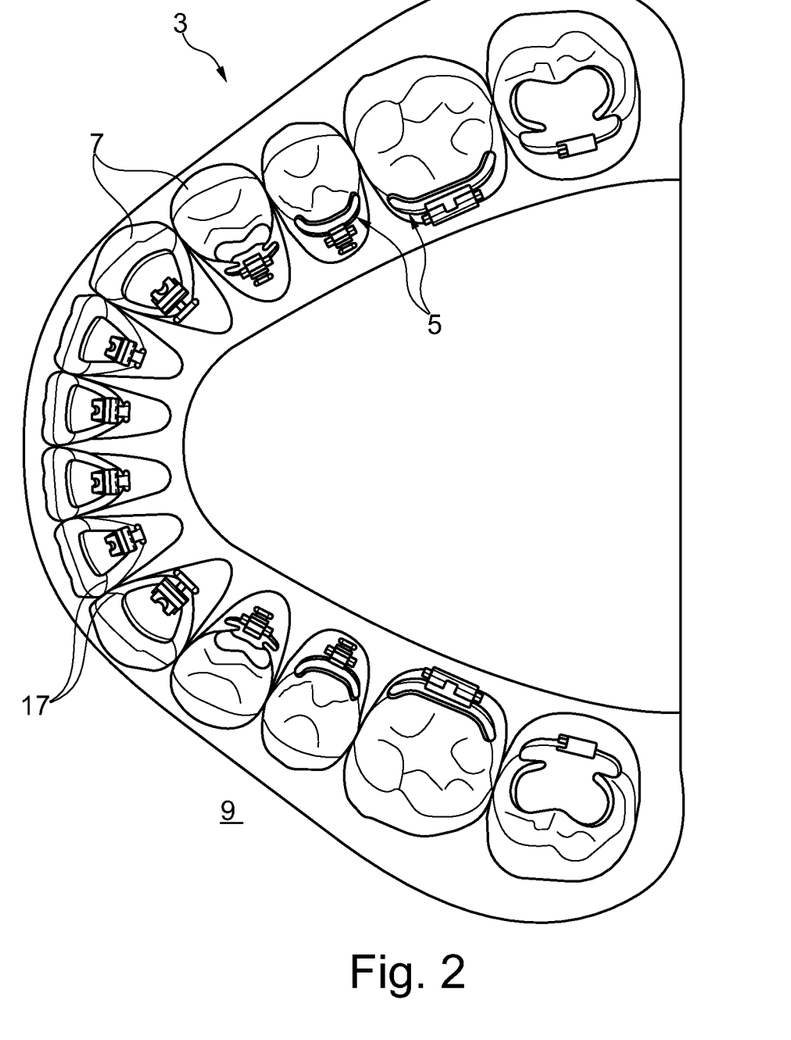
FIG. 2 shows a top view on the target set-up of FIG. 1.

A photo is taken with the camera as soon as the optics of the camera are set in focus to the slot plane of the lingual brackets 5 of the target set-up 3. FIG. 2 schematically shows the photo of the target set-up 3 of FIG. 1 from the top view.

In a next step, the photo is transferred from the camera, in this instance a digital camera, into a computer and there processed on the screen as follows, using a self-made software. The purpose of the software is mainly to identify, to determine and then to output the position of the individual slots. The process unfurls as below:

The patient is first of all inputted in the software, with his patient-specific data, such as for instance his name and date of birth. Then it is specified whether the photo of a target set-up of a lower jaw or of an upper jaw shall be processed. In this instance, it is specified that the photo of a target set-up 3 of a lower jaw shall be processed and the storage location of the photo on the computer is indicated, whereat the photo is loaded into the software.

Figure 3:
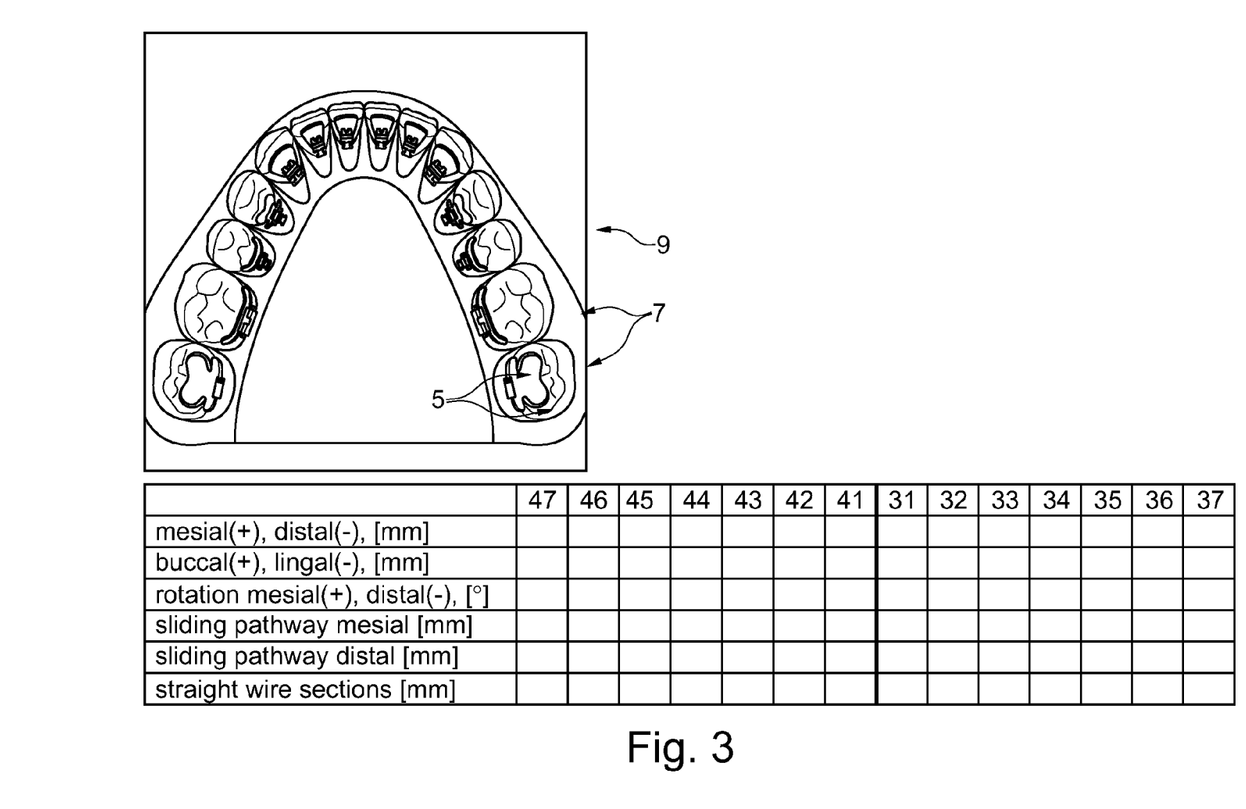
FIG. 3 shows a screen shot of a software for processing the top view of FIG. 2.

FIG. 3 is represented as below on the screen. The screen is divided in two sections: the photo of FIG. 2 is represented in the upper half (a two-dimensional image 9 of the target set-up with brackets in the top view). The lower half includes a matrix in which a column is provided for every tooth of the lower jaw (from 47 via 41 and 31 to 37). Individual parameters are listed line-by-line for each of these teeth in a further column (in FIG. 3 leftmost) for which parameters respective values can be inputted for the individual teeth, as described further down.

In a next step, the user clicks in the matrix on the number of the tooth for which he would like to identify the slot of the corresponding bracket in the photo, i.e. the user clicks for instance on the number "47" in the matrix in order then to establish the position of the slot for said tooth. The software knows now for which tooth the position of the slot of the bracket arranged on the tooth should be identified.

The corresponding brackets from different manufacturers with their respective slot dimensions are stored in the software for every tooth and the software asks the user in a next step which bracket from which company is arranged on the tooth inasmuch as firstly the manufacturer and then the bracket model is interrogated from the user. Said step is completed once the user has indicated to the software which bracket type from which manufacturer is arranged on the tooth. The software knows now which bracket with which slot dimensions is associated with the tooth.

In a next step, the user clicks on the bracket of the tooth 47 in the photo illustrated above in FIG. 3 to communicate the rough position of the bracket to the software.

Figure 4:
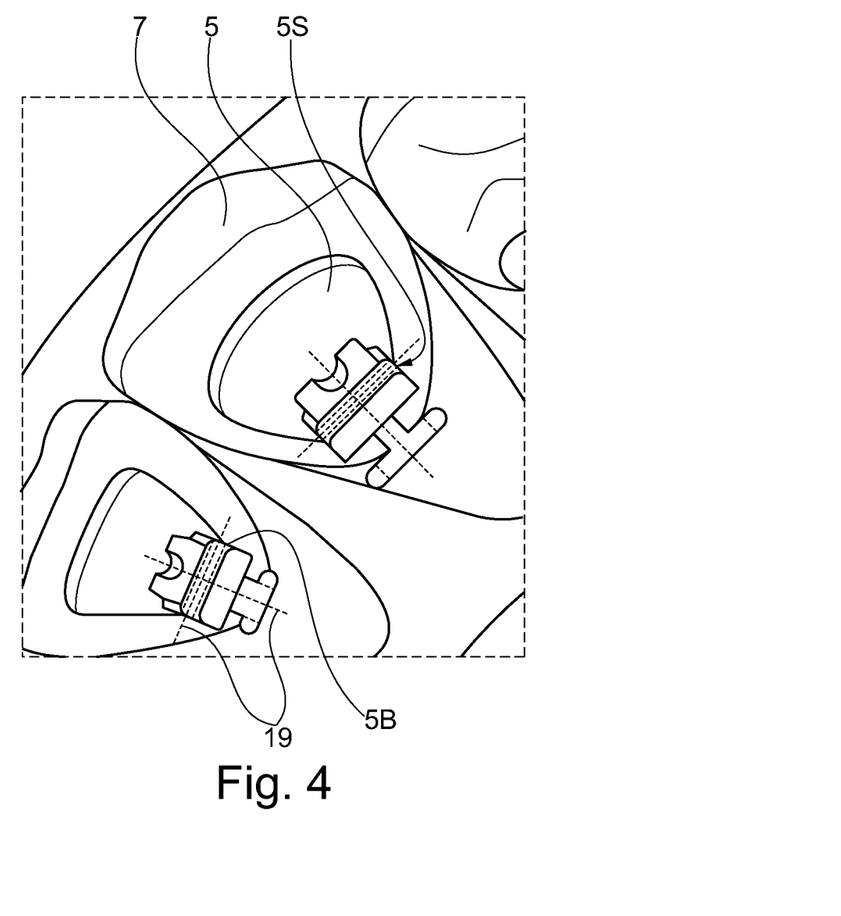
FIG. 4 shows an enlarged cut-out of FIG. 3, wherein additionally orientating aids for identification of the slots of the brackets are represented.

The software knows now on which place for which tooth which bracket is roughly sitting and it overlays at that location a base slot body 5B of the corresponding bracket 5 and a corresponding hair cross 19, see FIG. 4. The base slot body 5B generally reproduces the inner contour of the slot 5S of the bracket 5 and is a rectangle in this instance. Both lines of the hair cross 19 run respectively parallel to a short or long side of the rectangular base slot body 5B and the centre of hair cross 19 lies in the centre of gravity of the base slot body 5B.

The hair cross 19 provides guidance to position the base slot body 5B in the slot 5S of the bracket 5 of the tooth 47 in a next step, manually and as appropriate, i.e. to cover the inner contour of the slot 5S of the bracket 5 in the photo with the base slot body 5B. For this purpose, the base slot body 5S is moved and rotated on the photo using the mouse until the base slot body 5S covers the inner contour of the slot 5S in the photo, as shown for instance in FIG. 4 for the teeth 42 and 43.

Since the photo of the target set-up 3 is taken in a defined focal plane of the optics of the camera, the graduation of the illustration of the same in the photo is known and the base slot body 5B is matched with said graduation in the software thereby resulting in the cover of the base slot body 5S and the slot 5S in the photo.

The position of the slot 5S is now defined using the base slot body 5B for the bracket 5 of the tooth 47 and the corresponding data are stored automatically in the software. The data stored in the software include at least: tooth 47 and position as well as the dimension of the slot 5S. Optionally, the bracket type and bracket manufacturer can also be stored in memory.

The steps previously described for identification of the position of the slot 5S using the base slot body 5B for the tooth 47 are repeated subsequently for every tooth of the lower jaw to be treated whereby the position of every slot 5S is identified.

Once the identification of the position of all slots 5S has been finished, the matrix represented below in FIG. 3 offers the opportunity to modify for every slot of a bracket of every tooth, the value of the parameters listed there:

If it is desirable in an example to move the position of the slot mesially or distally, the desirable value can be inputted in mm into the second row of the table represented below in FIG. 3, a value which is desired additionally.

Analogically, the slot position can be displaced buccally or lingually with an input in the third row of the table represented below in FIG. 3.

An input into the fourth row of the table represented below in FIG. 3 enables to rotate the slot around its centre in mesial or distal direction wherein to do so the desirable angle should be inputted in [°], which is desired additionally.

If it is desired in a further example that the wire 1 has a longer sliding pathway in the slot 5S of the bracket 5 of the tooth 47, the desired value can be inputted in mm in the column 47 in the line "sliding pathway mesially" (fifth row), which value which is desired additionally.

Analogically, if a longer sliding path is desired distally, the corresponding value can be inputted into the next (sixth) row, which value which is desired additionally.

when all the necessary corrections are inputted into the matrix, the identification of the position of the slots 5S and the necessary corrections thereof are completed. Upon the user's request, the software now writes all data into a file in a next step. The file hence includes at least for every tooth to be treated: the number of the tooth, the position as well as the dimension of the slot 5S of the corresponding bracket 5, inclusive of the correction values performed. Optionally, also additional data can be stored in memory, such as for instance the name of the patient, the bracket type and the bracket manufacturer.

As a next step, using this file a baking mould 11 is created (in this instance an aluminium plate) for the orthodontic wire 1 as follows:

An aluminium plate with the dimensions 79.5 mm×79.5 mm×2.5 mm is inserted into a CNC milling machine and fixed there. The aluminium plate includes six flat surfaces.

The aforementioned file (with the data regarding the position etc. of the slots) is loaded into the CNC milling machine.

Figure 5A:
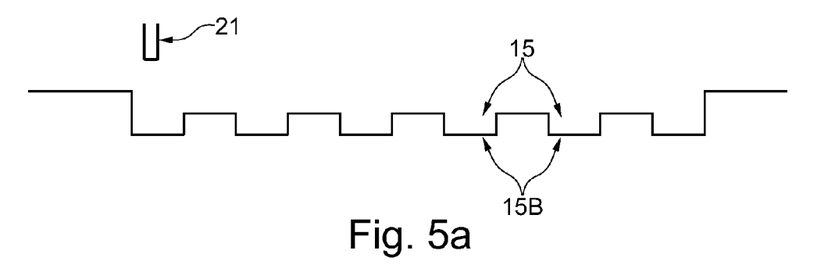
FIG. 5a shows a schematic cross-sectional view of a baking mould in a development along a curved line and a milling head wherein free spaces are milled into the baking mould for the orthodontic wire.

Using a cylindrical milling head 21 with a width of 2 mm the arc form is milled into the aluminium plate, see FIG. 5a, showing a development of the arc form. The milling head 21 does not mill the arc form into the aluminium plate at a certain height, but leaves areas corresponding to the slots and in which the orthodontic wire 1 is to be held during the baking process, the so-called wire-fixing portions 13. FIG. 5a shows accordingly several free spaces 15 and elevated areas between the free spaces 15.

Once the milling head 21 has milled the arc form into the aluminium plate, it is automatically exchanged against another head with a smaller diameter which is slightly larger than that of the orthodontic wire 1.

This milling head mills into the elevated areas formed between two free spaces a bottom 13B whereby wire-fixing portions 13 are formed between the free spaces 15 in which the orthodontic wire 1 is held during the baking process thereof.

Figure 5B:
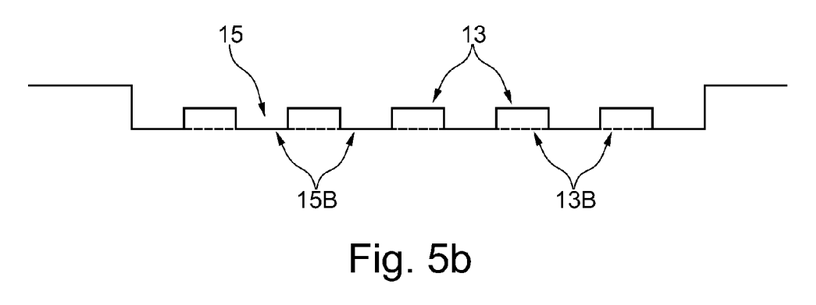
FIG. 5b shows the view of FIG. 5a), wherein however wire-fixing portions are milled between the free spaces.

The bottoms 13B of the wire-fixing portions 13 and the bottoms 15B of the free spaces 15 then lie on one height, as shown by FIG. 5b.

Figure 6:
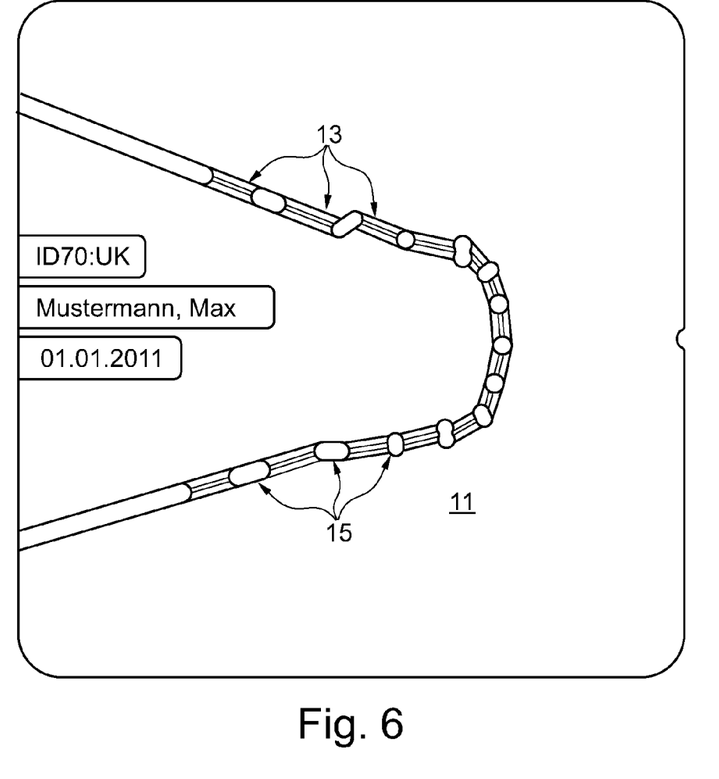
FIG. 6 shows a top view onto a finished baking mould.

The aluminium plate then presents wire-fixing portions 13 by which the orthodontic wire 1 can be held, and free spaces 15, inside which the orthodontic wire 1 cannot be held. The wire-fixing portions 13 correspond to the later slots 5S of the brackets. The aluminium plate this way forms the baking mould 11 for the orthodontic wire 1. FIG. 6 shows the finished baking mould in a top view with its wire-fixing portions 13 and its free spaces 15. Moreover, the date of creation of the baking mould as well as the name and the first name of the patient and also a case number are milled into the baking mould 11 wherein the latter also includes the information UK to indicate that it concerns the lower jaw model of the patient.

Once the baking mould 11 has been created, the orthodontic wire 1 is inserted manually into the baking mould 11, i.e. the orthodontic wire 1 is inserted into the wire-fixing portions 13 and then rests flat on the bottoms 13B and 15B.

Figure 7:
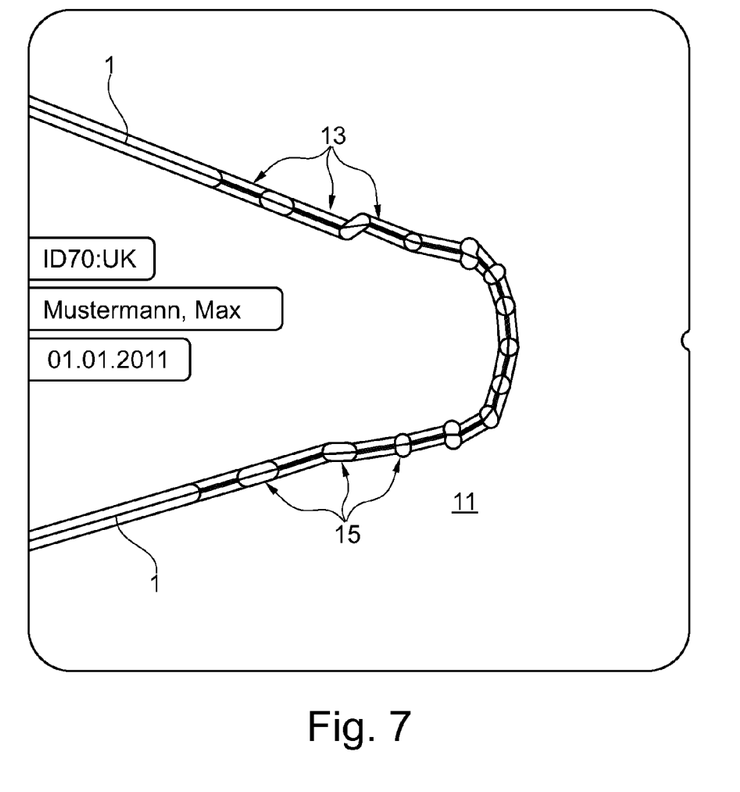
FIG. 7 shows the baking mould of FIG. 6 into which an orthodontic wire is inserted.

FIG. 7 shows the baking mould of FIG. 6 into which an orthodontic wire 1 is inserted additionally. The distal wire sections protruding after the last wire-fixing section 13 (in FIG. 7 below) can be shortened by the therapist as required.

In a next step, the orthodontic wire 1 arranged in this manner in the baking mould 11 is baked in a baking oven in the baking mould 11 by which the orthodontic wire 1 is programmed to adopt said geometry, i.e. the desired target geometry. The orthodontic wire 1 can now be inserted into an orthodontic apparatus of a patient.

By "orthodontic apparatus" is meant in the context of the present application the arrangement of lingual or buccal brackets on teeth of a patient to be treated orthodontically. The target geometry is the geometry of the orthodontic wire, in which the treating orthodontist wishes to have the orthodontic wire so that in the state inserted into the orthodontic apparatus it causes the desired movement of the teeth to be treated.

In step 1b) preferably lingual brackets are arranged on the teeth to be treated. Alternatively, buccal brackets can also be arranged on the teeth.

LIST OF REFERENCE SIGNS

1 orthodontic wire
3 patient-specific target set-up of a lower jaw of a patient
5 (lingual) bracket
5B base slot body
5S slot of the bracket
7 tooth
9 two-dimensional image of the target set-up with brackets in elevation
1 baking mould
13 wire-fixing section
13B bottom of a wire-fixing section
15 free space
15B bottom of a free space
17 laser band
19 hair cross
21 milling head

The invention claimed is:
1. Method for shaping an orthodontic wire (1) made of a shape memory material into a target geometry for fitting insertion into a patient-specific orthodontic apparatus with the following steps:
    a. creating a patient-specific target set-up of the upper jaw or lower jaw of the patient,
    b. placing brackets (5) on teeth to be treated in the target set-up, c. preparing a two-dimensional image of the target set-up with brackets (5) in a plan view,
d. loading the image into a data processing unit,
e. identifying the position of the slots (5S) of the brackets (5) in the image,
f. exporting data on the position of the slots (5S) from the data processing unit,
g. creating a baking mould (11) for the shape memory wire, wherein wire-fixing portions (13) in the baking mould are generated using the data, portions that hold the wire in the areas corresponding to the slots (5S) during the baking process,
h. inserting the wire into the baking mould and
i. baking the wire.

2. Method of claim 1, characterised in that in step 1a) a target set-up of plaster or a virtual target set-up is generated.

3. Method according to claim 1, characterised in that in step 1b) lingual brackets are arranged on the teeth of the target set-up to be treated.

4. Method according to claim 1, characterised in that in step 1c) a two-dimensional photo is prepared.

5. Method of claim 4, characterised in that for step 1c) a light band is projected into the target set-up, a band showing the focal plane of the optics for preparing the photo and in that the light band is projected into the slot plane, whereby the slots (5S) are represented clearly in the image.

6. Method according to claim 4, characterised in that in step 1c) a digital photo is prepared as a reproduction.

7. Method according to claim 4, characterised in that the two-dimensional photo is prepared with a camera with optics.

8. Method according to claim 1, characterised in that in step 1d) a digital photo or a scan of an analogue photo is loaded into the data processing unit.

9. Method according to claim 1, characterised in that a computer is used as a data processing unit.

10. Method according to claim 9, characterised in that the computer is a desktop computer.

11. Method according to claim 1, characterised in that the identification in step 1e) takes place manually or automatically.

12. Method according to claim 1, characterised in that after the identification in step 1e) the position of at least one slot (5S) is modified manually in the occlusal plane.

13. Method according to claim 12, characterised in that the position of the at least one slot (5S) is modified after the mesial, distal, lingual or buccal, by rotation or combinations thereof.

14. Method according to claim 1, characterised in that after the identification in step 1e) the length of at least one slot is increased or decreased mesially and/or distally.

15. Method according to claim 1, characterised in that exporting in step 1f) is the writing of the data into a computer file.

16. Method according to claim 1, characterised in that in step 1g) a baking mould is created of a metal plate.

17. Method of claim 16, characterised in that in step 1g) the wire-fixing portions for the wire are milled into the metal strip and respectively a free space is milled for the wire between neighbouring wire-fixing portions, in which the wire is not held.

18. Method of claim 17, characterised in that the bottoms of the wire-fixing portions and the bottoms of the free spaces are milled at the same height by which the wire may be inserted flat into the baking mould.

19. Method according to claim 16, characterised in that the metal plate is one of a steel or aluminium plate.

20. Method according to claim 1, characterised in that the wire in step 1h) is inserted manually into the baking mould.

21. Method according to claim 1, characterised in that the identification in step 1e) is accomplished using morphing algorithms.

* * * * *